United States Patent
Borders et al.

(10) Patent No.: US 6,644,837 B2
(45) Date of Patent: Nov. 11, 2003

(54) CONTROLS FOR A SURGICAL LIGHT APPARATUS

(75) Inventors: Richard L. Borders, Cincinnati, OH (US); Dennis C. Coon, Erie, PA (US); Ronald P. Krahe, Girard, PA (US); John M. Bulko, Apex, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 10/095,229

(22) Filed: Mar. 11, 2002

(65) Prior Publication Data

US 2002/0089857 A1 Jul. 11, 2002

Related U.S. Application Data

(62) Division of application No. 09/050,534, filed on Mar. 30, 1998, now Pat. No. 6,402,351
(60) Provisional application No. 60/079,667, filed on Mar. 27, 1998.

(51) Int. Cl.$^7$ .............................................. F21V 21/08
(52) U.S. Cl. ...................... 362/399; 362/294; 362/295; 362/804; 362/373; 362/285; 362/287; 362/269
(58) Field of Search .................................. 362/399, 294, 362/804, 295, 373, 285, 289, 33, 85, 271, 272, 268, 269, 287

(56) References Cited

U.S. PATENT DOCUMENTS

| | | |
|---|---|---|
| 3,075,071 A | 1/1963 | Lauterbach |
| 3,887,801 A | 6/1975 | Ilzig et al. |
| 3,891,842 A | 6/1975 | Strusinski |
| 4,037,096 A | 7/1977 | Brendgord et al. |
| 4,159,511 A | 6/1979 | Dejone |
| 4,171,572 A | 10/1979 | Nash |
| 4,254,454 A | 3/1981 | Hardin, Jr. |
| 4,254,455 A | 3/1981 | Neal, Jr. |
| 4,280,167 A | 7/1981 | Ellett |

(List continued on next page.)

FOREIGN PATENT DOCUMENTS

| | | |
|---|---|---|
| DE | 1 962 656 | 6/1971 |
| DE | 94 18 339 | 2/1995 |
| WO | 95/16875 | 6/1995 |

OTHER PUBLICATIONS

Berchtold Corporation, "Chromophare C–571 Superior lighting technology is the secret of our success", Feb. 1995, 8 pages.

Berchtold Corporation, chromphare C–570 Service Manuel, date unknown, 2 pages.

*Primary Examiner*—Sandra O'Shea
*Assistant Examiner*—Mark Tsidulko
(74) *Attorney, Agent, or Firm*—Barnes & Thornburg

(57) ABSTRACT

A surgical lighthead includes a reflector, a lens coupled to the reflector, and a handle located adjacent the lens. The handle defines an air passage to facilitate installation of a shield over the handle. A lamp assembly includes a support and at least one bulb located on the support between the reflector and the lens. Tubes are mounted in an interior region of the lighthead between the reflector and the lens, and rods are configured to engage the support. Each rod extends through the support and into a corresponding tube. The rods include at least one threaded portion configured to secure the lamp assembly within the interior region. The rods are slidable relative to the tubes upon disengagement of the threaded portions of the rods to permit the lamp assembly to move out of the interior region of the lighthead. The rods include stops to prevent separation of the lamp assembly from the lighthead. A controller turns the bulb on and off and adjusts the intensity level of light emitted from the bulb. Spaced apart first and second displays are coupled to the controller. Each displays an indication of the intensity level of the bulb.

25 Claims, 10 Drawing Sheets

U.S. PATENT DOCUMENTS

| | | | |
|---|---|---|---|
| 4,288,844 A | 9/1981 | Fisher et al. | |
| 4,316,237 A | 2/1982 | Yamada et al. | |
| 4,380,794 A | 4/1983 | Lawson | |
| 4,395,750 A | 7/1983 | Scheidemann et al. | |
| 4,400,765 A | 8/1983 | Kochem | |
| 4,514,062 A | 4/1985 | Fitzgerald | |
| 4,517,632 A | 5/1985 | Roos | |
| 4,578,575 A | 3/1986 | Roos | |
| 4,600,979 A | 7/1986 | Fisher et al. | |
| 4,617,619 A | 10/1986 | Gehly | |
| 4,622,625 A | 11/1986 | Becker et al. | |
| 4,844,252 A | 7/1989 | Barron et al. | |
| 4,878,156 A | 10/1989 | Hallings et al. | |
| 4,884,008 A | 11/1989 | Bossler et al. | |
| 4,937,714 A | 6/1990 | Witt | |
| 4,937,715 A | 6/1990 | O'Shea et al. | |
| 4,974,288 A | 12/1990 | Reasner | |
| 4,975,817 A | 12/1990 | Reimers | |
| 4,994,945 A * | 2/1991 | O'Shea et al. | 362/268 |
| 5,001,616 A | 3/1991 | Gehly et al. | |
| 5,023,515 A | 6/1991 | Olon et al. | |
| 5,036,446 A | 7/1991 | Quintanilla et al. | |
| 5,065,296 A | 11/1991 | Cude | |
| 5,067,064 A | 11/1991 | Gehly et al. | |
| 5,099,405 A * | 3/1992 | Gehly et al. | 362/400 |
| 5,156,456 A | 10/1992 | Hoftman et al. | |
| 5,165,786 A * | 11/1992 | Hubert | 362/287 |
| 5,178,452 A | 1/1993 | Scholz | |
| 5,188,454 A | 2/1993 | Quintanilla et al. | |
| 5,199,785 A | 4/1993 | Scholz | |
| 5,235,470 A | 8/1993 | Cheng | |
| 5,331,530 A | 7/1994 | Scholz | |
| 5,355,292 A | 10/1994 | Hoftman et al. | |
| 5,383,105 A | 1/1995 | Agut | |
| 5,469,600 A * | 11/1995 | Sandel | 16/421 |
| 5,485,319 A | 1/1996 | Lemons | |
| 5,488,696 A | 1/1996 | Brosnan | |
| 5,539,626 A | 7/1996 | Scholz | |
| 5,568,967 A | 10/1996 | Sikkens et al. | |
| 5,599,093 A | 2/1997 | Hoftman et al. | |
| 5,604,955 A | 2/1997 | Horan | |
| 5,871,522 A | 2/1999 | Sentilles | |
| 6,012,821 A | 1/2000 | Yeaney et al. | |
| D421,148 S | 2/2000 | Borders | |
| D421,507 S | 3/2000 | Borders et al. | |
| 6,132,062 A | 10/2000 | Borders et al. | |
| 6,176,597 B1 | 1/2001 | Smith | |
| D437,957 S | 2/2001 | Borders et al. | |

* cited by examiner

CONTROLS FOR A SURGICAL LIGHT APPARATUS

CROSS-REFERENCE TO RELATED APPLICATIONS

This application is a division of U.S. Ser. No. 09/050,534 filed Mar. 30, 1998, now U.S. Pat. No. 6,402,351 which claims benefit of provisional application No. 60/079,667 filed Mar. 27, 1998.

BACKGROUND AND SUMMARY OF THE INVENTION

The present invention relates to a surgical light apparatus. More particularly, the present invention relates to improved controls for the operation of a surgical light apparatus for generating light at a surgical site.

Surgical lights used in hospital operating rooms to illuminate surgical sites on patients are known. Many surgical lights are suspended from a ceiling of a hospital room by arm mechanisms which are movable to permit adjustment of the location of the surgical light relative to the patient. It is common for surgical lights to be placed in a position behind a surgeon such that the surgeon's head is located between the surgical light and the surgical site. Surgical lights having a dome-shaped reflector to reflect light toward the surgical site around the head of the surgeon are known. It is desirable for surgical lights to provide a high illuminance level, to shine light deeply into a patient's body cavity, and to resist shadowing caused by interference from personnel and instruments.

Surgical lights typically include a housing surrounding a reflector and a lens coupled to the housing and facing toward the surgical site. A handle typically extends down from a center portion of the lens to permit the surgeon to adjust the position of the light during the surgical procedure. The surgeon can also change a pattern size of reflected light generated by the surgical light by rotating the handle to move the light source toward and away from the reflector.

At least the handle and the lens of the surgical light are located in a sterile field prepared for the surgical procedure. In other words, a bottom portion of the surgical light including the lens and the handle must be sterilized prior to a surgical procedure by wiping, cleaning or other means. Often a separate, disposable latex cover or shield is placed over the handle prior to the surgical procedure to provide a sterile field on the handle.

Intensity controls for conventional surgical lights are located on wall boxes spaced apart from the surgical light or on a portion of the surgical light outside of the sterile field. The surgical light apparatus of the present invention advantageously locates all of the light controls inside the sterile field. This allows the surgeon or other sterile personnel in the surgical suite to adjust the position of the surgical light, to adjust the focus of the light by turning the handle, and also to operate the on/off and intensity or brightness controls for the light from within the sterile field during a surgical procedure.

According to one aspect of the present invention, a surgical light apparatus includes a lighthead having a sterile field thereon, a bulb located within the lighthead, a controller coupled to the bulb, and an actuator coupled to the controller to adjust an intensity of light emitted from the bulb. The actuator is located in the sterile field on the lighthead.

The lighthead illustratively includes a reflector, a lens, and a handle located adjacent the lens. In the illustrated embodiment, the actuator is located on the handle. The handle is illustratively configured to extend outwardly from a center portion of the lens. The actuator illustratively may be a push button actuator, rocker switch, or a squeezable actuator.

In the illustrated embodiment, the actuator is configured to engage a switch coupled to the controller. The controller is illustratively configured to turn the bulb on and off and to adjust the intensity level of the bulb between a minimum intensity level setting (L1) and a maximum intensity level setting (Ln) in a predetermined sequence based on each switch actuation by the actuator.

A panel located adjacent the sterile handle, in the sterile field, provides an intensity level display. The display also includes a relamp indicator light which notifies the user that the main light bulb has failed and that a backup or auxiliary bulb is currently in use. In addition, the display provides a standby light to indicate that power is supplied to the light. The surgical light apparatus of the present invention provides duplicate sets of displays on opposite sides of the surgical light so that the surgeon can view one of the displays regardless of the orientation of the surgeon relative to the light.

According to another aspect of the present invention, a surgical light apparatus includes a lighthead including a bulb, a lens, a controller for turning the bulb on and off and for adjusting an intensity level of light emitted from the bulb, a first display, and second display spaced apart from the first display. The first display and second display are each coupled to the controller and are each configured to display an indication of the intensity level of the bulb.

The illustrated first and second displays are spaced apart by about 180°. The first and second displays illustratively each include a plurality of LEDs. Each LED indicates a different light intensity level for the bulb.

According to yet another aspect of the present invention, a surgical light apparatus includes a lighthead having a reflector, a lens coupled to the reflector, a plurality of tubes mounted in an interior region of the lighthead between the reflector and the lens, a lamp assembly including a support and at least one bulb, and a plurality of rods configured to engage the support. Each rod is configured to extend through the support and into a corresponding tube. The rods include at least one threaded portion configured to secure the lamp assembly within the interior region. The rods are slidable relative to the tubes upon disengagement of the threaded portion of the rods to permit the lamp assembly to move out of the interior region of the lighthead. The rods each are formed to include a stop to prevent separation of the lamp assembly from the lighthead. In the illustrated embodiment, the stops are threaded stops so that the rods can be removed upon rotation of the rods to permit separation of the lamp assembly from the lighthead.

The sterile handle of the present invention is removable for cleaning or autoclaving. The actuation button is illustratively integrated into the end of the sterile handle, but the electrical switch resides inside the light core to facilitate cleaning.

The sterile handle controls of the present invention, located in the sterile field, provide the surgeon or other sterile personnel full control over the surgical light without the need to access distant controls located on a portion of the surgical light outside the sterile field or located on a wall in the surgical suite. The sterile handle controls can be used alone and do not require wall mounted controls and related installation and wiring costs.

However, the surgical light apparatus of the present invention also provides a wall mounted control panel coupled to the surgical light apparatus for use by non-sterile personnel in the surgical suite. The wall control panel can accommodate a plurality of light systems, typically up to three lights per panel. The wall control panel functions in a manner identical to the sterile handle controls. The wall control panel also includes displays for light intensity, relamp indicator, and standby mode the same as those located on the surgical light. The sterile handle controls and the wall control panel use the same controller located above the surgical light.

The surgical light apparatus of the present invention is also designed to facilitate maintaining a sterile field adjacent the handle. In particular, the handle is configured to facilitate installation of a standard disposable sterile handle cover or shield. The handle is configured with an air passage to permit air which would otherwise be trapped between the shield and the handle to exit through the handle and into an interior region of the surgical light apparatus.

According to a further aspect of the present invention, a surgical light apparatus includes a reflector, a lens coupled to the reflector, a bulb located between the reflector and the lens, and a handle located adjacent the lens. The handle is configured to define an air passage to facilitate installation of a shield over the handle.

In the illustrated embodiment, the handle includes a longitudinal axis and a distal end. The air passage is formed in the distal end of the handle and extends along the longitudinal axis. The air passage illustratively extends into an interior region of the surgical light apparatus formed between the reflector and the lens. The distal end of the handle is enlarged to retain the shield on the handle.

According to an additional aspect of the present invention, a surgical light apparatus includes a lighthead having a reflector and a lens, a lamp assembly including a support and at least one bulb located on the support, and a lamp position adjustment mechanism which is coupled to the support and configured to adjust a position of the lamp assembly relative to the reflector to change a pattern size of reflected light emitted from the surgical light apparatus. The apparatus also includes a filament shield mounted in an interior region of the lighthead between the reflector and the lens to block light from passing from the at least one bulb directly through the lens. The filament shield is configured to move with the lamp assembly as the position of the lamp assembly is adjusted by the lamp position adjustment mechanism. The filament shield is also configured to remain in the interior region of the lighthead when the lamp assembly is removed from the interior region to change the bulb or for servicing.

In the illustrated embodiment, a frame is mounted to the lighthead between the reflector and the lens. The filament shield is coupled to the frame. The frame includes a stop, and the filament shield is illustratively mounted between the stop and the reflector to provide a limit position for movement of the filament shield toward the lens. The filament shield is spring biased against the stop. The illustrated filament shield includes an inner flange configured to engage the support of the lamp assembly. The lamp assembly is configured to move the filament shield away from the stop as the position of the lamp assembly is adjusted by the lamp position adjustment mechanism.

The illustrated lamp assembly includes a primary bulb and a redundant bulb. The filament shield is configured to block light from both the primary bulb and the redundant bulb from passing directly through the lens. The illustrated filament shield includes a bottom plate and an outer sidewall extending upwardly from an edge of the bottom plate.

Additional features and advantages of the present invention will become apparent to those skilled in the art upon consideration of the following detailed description of illustrated embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
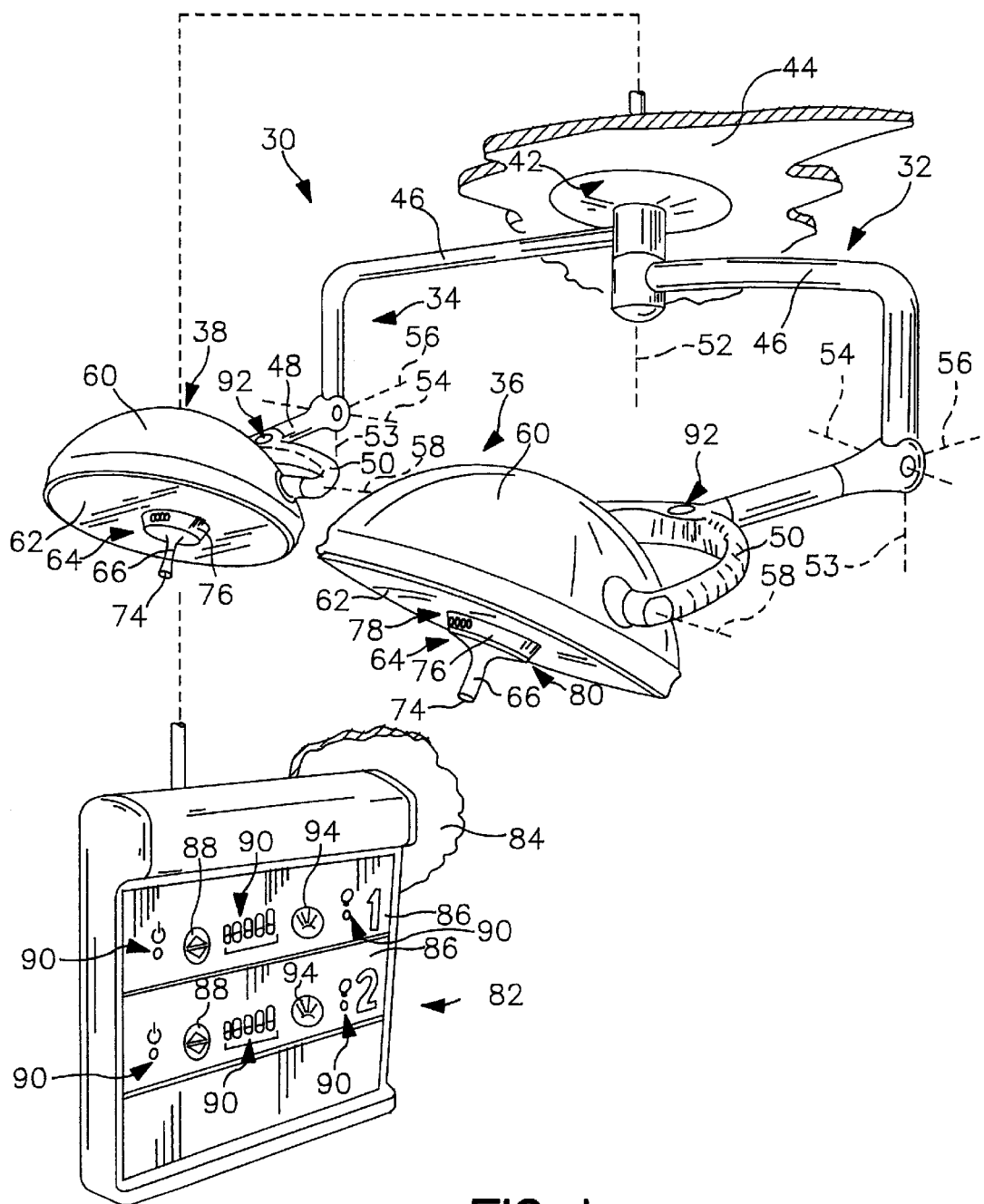
FIG. 1 is a perspective view of a surgical light apparatus in accordance with the present invention showing a first surgical lighthead suspended from a ceiling of a hospital room by a first arm assembly, a second surgical lighthead suspended from the ceiling of the hospital room by a second arm assembly, and a light-controller box mounted to a wall of the hospital room.

A surgical light system 30 includes a first arm assembly 32, a second arm assembly 34, a first lighthead 36 coupled to first arm assembly 32, and a second lighthead 38 coupled to second arm assembly 34 as shown in FIG. 1. First and second arm assemblies 32, 34 each couple to a common mounting apparatus 42 which is configured to mount to suitable support structure (not shown) associated with a ceiling 44. It is understood that the first and second lightheads 36, 38 may be mounted to any suitable support structure such as on a wall or separate stand. Each arm assembly 32, 34 includes an L-shaped upper arm 46, a lower arm 48, and a yoke 50. Each upper arm 46 is independently pivotable relative to mounting apparatus 42 about a vertical pivot axis 52. Each lower arm 48 is pivotable relative to the respective upper arm 46 about a respective horizontal pivot axis 54 and about a respective vertical pivot axis 53 that is spaced from pivot axis 52. In addition, each yoke 50 is pivotable relative to the respective lower arm 48 about a respective pivot axis 56 and each of lightheads 36, 38 is pivotable relative to the respective yoke 50 about a respective pivot axis 58. Thus, arm assemblies 32, 34 and lightheads 36, 38 are movable to a variety of positions relative to ceiling 44.

Figure 2:
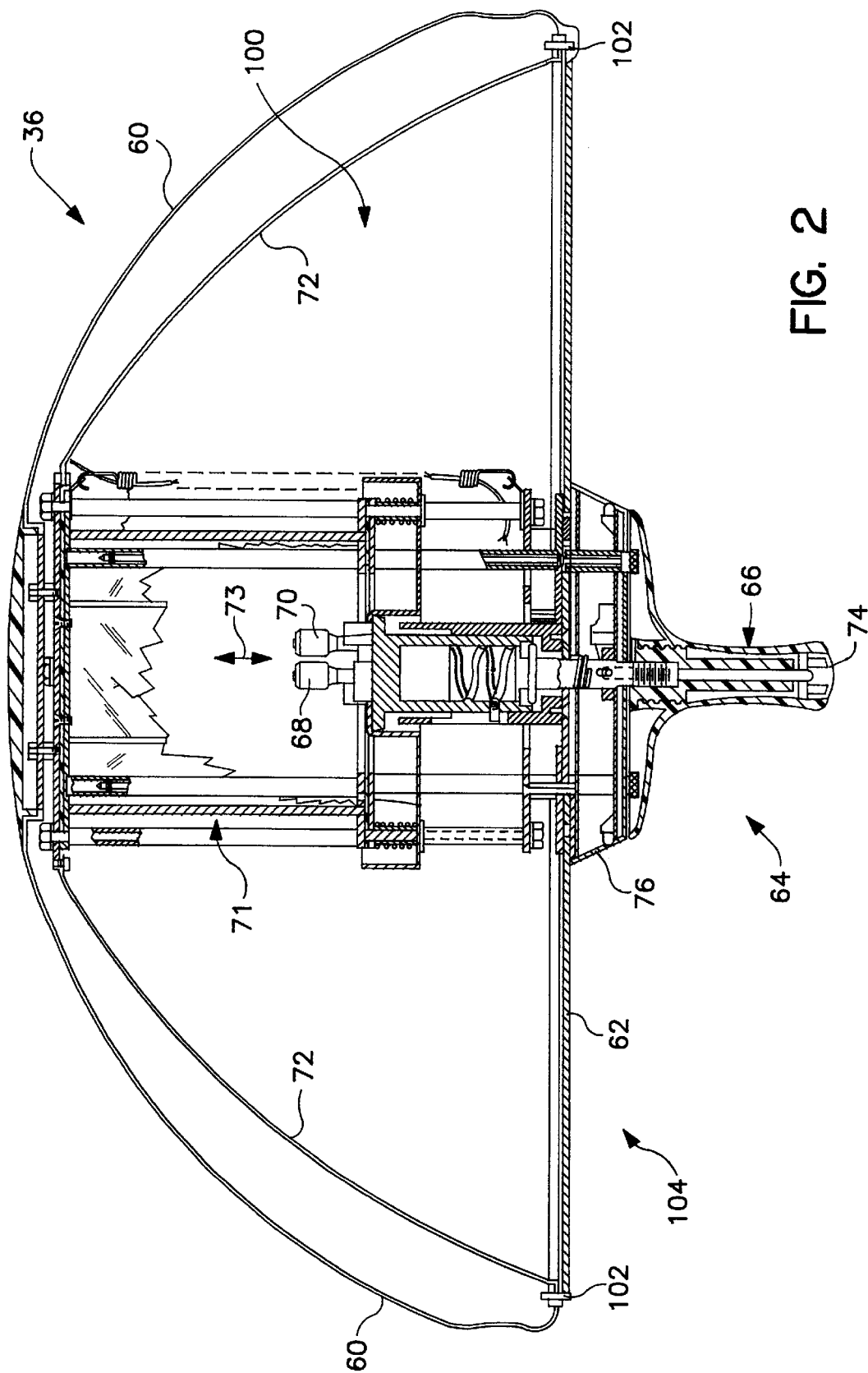
FIG. 2 is a sectional view of the first surgical lighthead of FIG. 1, taken along line 2—2, showing a dome-shaped outer cover, a dome-shaped reflector surrounded by the outer cover, a lens coupled to the outer cover, a lamp assembly surrounded by the reflector and lens, and a handle assembly coupled to the lamp assembly.

Each lighthead 36, 38 includes a dome-shaped housing 60, a lens 62 through which light shines from the respective lighthead 36, 38, and a handle assembly 64 as shown in FIG. 1. Each handle assembly 64 includes a handle 66 which is grasped by a surgeon to move the respective lighthead 36, 38 and associated arm assembly 32, 34 to a desired position. Each lighthead 36, 38 includes a lamp assembly 69 having a main light bulb 68 and a redundant or auxiliary light bulb 70 as shown in FIG. 2 with reference to surgical lighthead 36. In addition, each lighthead 36, 38 includes a reflector 72 that reflects light emanating from either bulb 68 or bulb 70 to illuminate a surgical site on a patient. Auxiliary bulb 70 remains in an off state until main light bulb 68 burns out and then auxiliary bulb 70 turns on automatically. Thus, only one of bulbs 68, 70 is on at any instance in time when surgical light system 30 is in use. Each lighthead 36, 38 also includes a light absorption filter apparatus 71 as shown in FIG. 2 with reference to surgical lighthead 36. Light absorption filter 71 is fabricated from specially formulated glass which filters most of the near and intermediate infrared emissions from either of bulbs 68, 70.

The description below of lighthead 36 and the operation of lighthead 36 applies as well to lighthead 38 and the operation of lighthead 38 unless specifically noted otherwise. In addition, although surgical light system 30 includes two arm assemblies 32, 34 and two lightheads 36, 38 as shown in FIG. 1, it is within the scope of the invention as presently perceived for a different number of arm assemblies and corresponding lightheads to be provided. For example, a surgical light system having only one arm assembly and one corresponding lighthead and a surgical light system having three or more arm assemblies and three or more corresponding lightheads are possible.

Figure 3:
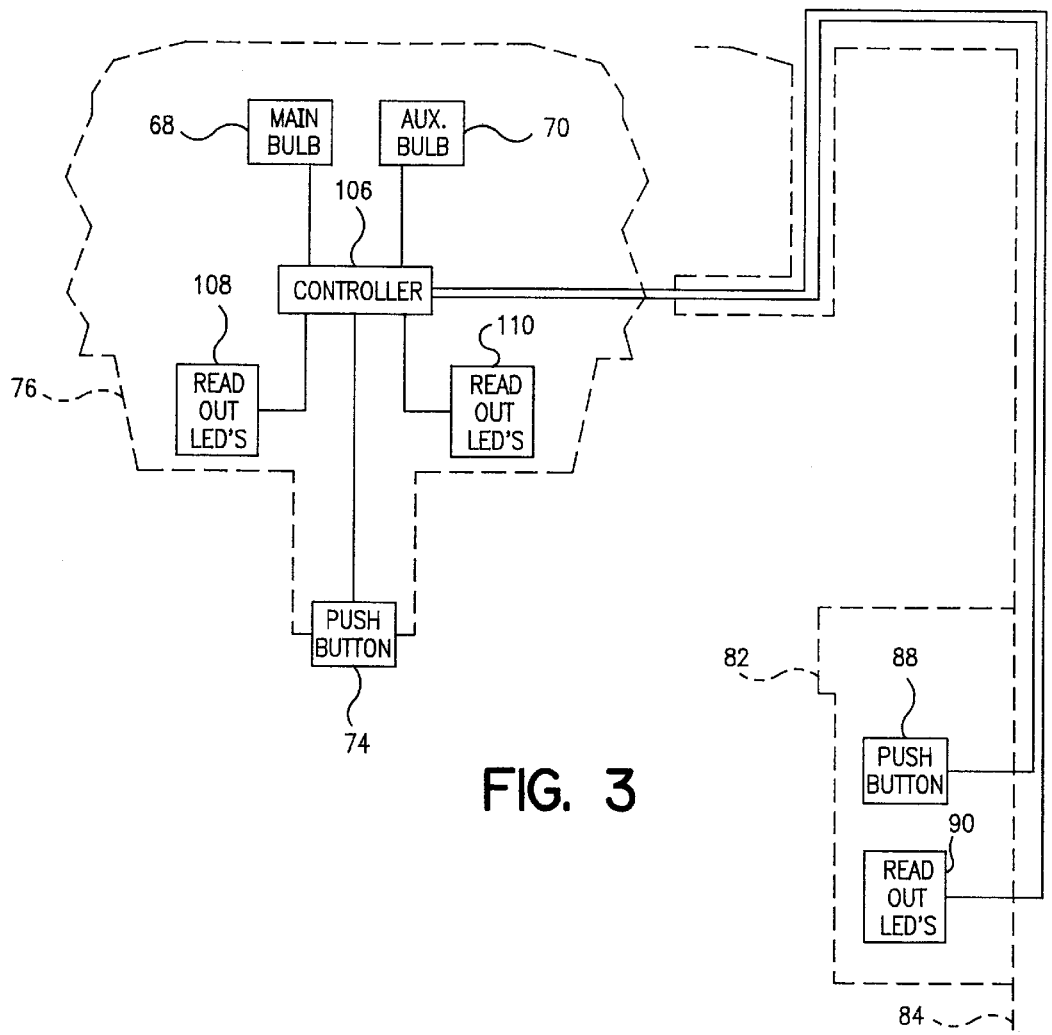
FIG. 3 is a diagrammatical view illustrating controls on the handle of the surgical light and on a light-controller panel mounted to the wall of the hospital room.

Handle 66 of each handle assembly 64 is rotatable to move main light bulb 68 and auxiliary light bulb 70 up and down relative to reflector 72 as illustrated by double headed arrow 73 in FIG. 3 to adjust the pattern size of reflected light that illuminates the surgical site. The pattern size may be thought of generally as the diameter of the area illuminated by the associated lighthead 36, 38. In addition, handle assembly 64 includes a button 74 at the bottom of handle 66 which is pressed to adjust the intensity level at which light emanates from bulbs 68, 70. Handle assembly 64 includes an escutcheon or light core panel 76 located above handle 66. Handle assembly 64 further includes a first set of LED's 78 and a second set of LED's 80 that are visible on respective sides of panel 76 to provide user information regarding whether one of bulbs 68, 70 is in use or in a standby mode, whether auxiliary bulb 70 or main bulb 68 is the operative bulb, and the intensity level at which light is emanating from the operative one of bulbs 68, 70. In preferred embodiments, bulbs 68, 70 are each tungsten halogen lamps.

Surgical light system 30 includes a controller box 82, shown in FIG. 1, which is mounted to a wall 84 or other suitable structure and which is coupled electrically to surgical lightheads 36, 38 to control the operation of bulbs 68, 70. Controller box 82 includes a control panel 86 having buttons 88 and sets of LED's 90 that are associated with each respective lighthead 36, 38. Each set of LED's 90 are arranged similarly and provide the same information as LED's 78, 80 of the respective lighthead 36, 38. In addition, each button 88 is pressed to change the light intensity of respective bulbs 68, 70 in the same manner that button 74 of the associated lighthead 36, 38 is pressed to change the light intensity of bulbs 68, 70. Thus, the operation of bulbs 68, 70 is controllable either with the respective handle assembly 64 or controller box 82. Surgical light system 30 optionally may include a task light 92, shown in FIG. 1, and controller box 82 optionally may include a button 94 that is pressed to turn task light 92 on and off.

Other features of surgical light system 30 are discussed and shown in detail in co-pending U. S. Pat. No. 6,176,597 entitled Reflector for Surgical Light Apparatus; U.S. Pat. No. 6,012,821 entitled Support Arm for a Surgical Light Apparatus; U.S. Pat. No. 6,443,596 entitled Surgical Lighting Apparatus with Improved Cooling; U. S. Pat. No. D 437,957 entitled Surgical Light Apparatus; U.S. Pat. No. 6,132,062 entitled Task Light for a Surgical Light Apparatus; U.S. Pat. No. D 421,148 entitled Handle for a Surgical Lighthead; and U.S. Pat. No. D 421,507 entitled Surgical Lighthead Cover, all filed Mar. 30, 1998, and all of which are incorporated herein by reference.

Referring to FIG. 2, the surgical lighthead 36 defines an interior region or enclosure 100 between lens 62 and reflector 72. Lens 62 and reflector 72 are coupled to outer housing 60 by suitable fasteners 102. Since the surgical light apparatus of the present invention is used in a surgical suite during a surgical procedure, a sterile field must be provided on the lighthead 36. The sterile field 104 shown in FIG. 2 is typically the area of lens 62 and handle assembly 64. Sterile field 104 may be maintained by wiping or cleaning the lens 62 and by sterilizing the handle assembly through cleaning or autoclaving and by providing a disposable, sterile cover or shield over the handle as discussed below with reference to FIGS. 8 and 9.

Advantageously, the controls of the surgical light apparatus are all located within the sterile field 104. As with conventional surgical lights, the operator can grip the handle 66 to move the light to a desired location, and the operator can rotate the handle to adjust the pattern size of reflected light that illuminates the surgical site. In addition, the present invention also permits the use of push button actuator 74 on handle 66 to turn the surgical light on and off and to adjust the intensity level at which light emanates from bulbs 68, 70.

Therefore, the sterile handle controls provide the surgeon or other sterile personnel full control over the surgical light without the requirement of accessing distant wall controls or controls located outside the sterile field of the surgical light apparatus. The handle controls can be used alone and it is not required to use the wall mounted controls which increase installation and wiring costs.

It is understood that an additional actuator button or a rocker switch can be used on the handle 66, if desired. In addition, another type of actuator such as a squeezable actuator may be used to control the on/off and intensity of the bulbs 68, 70.

FIG. 3 illustrates the control of the main bulb 68 and auxiliary bulb 70 by a controller 106 of the surgical light apparatus. The controller 106 is coupled to both the main bulb 68 and auxiliary bulb 70. As described in detail below, the controller 106 is also coupled to a switch controlled by the push button actuator 74 on the handle 66. Controller 106 also provides information to readout LED's 108 and 110 which provide two separate displays on opposite sides of light core panel 76. Providing the separate displays on opposite sides of the panel 76 permits the surgeon or other personnel to see the intensity level and other information provided by the display, regardless of the orientation of the lighthead 36.

The controller 106 is also coupled to the push button actuator 88 and the readout LED's 90 on controller box 82 mounted to wall 84. Therefore, the same display of the status of the surgical light is provided on the controller box 80 through readout LED's 90. Push button 88 can be used in a manner similar to push button 74 to control the on/off and intensity of the light emanating from main bulb 68 or auxiliary bulb 70.

It is understood that the surgical light apparatus may include either the controls on handle 66, the controls on controller box 82, or both sets of controls. In other words, the surgical light apparatus can operate with only the push button control 74 on the handle 66 or with only with the wall controller box 82, if desired.

Figure 4:
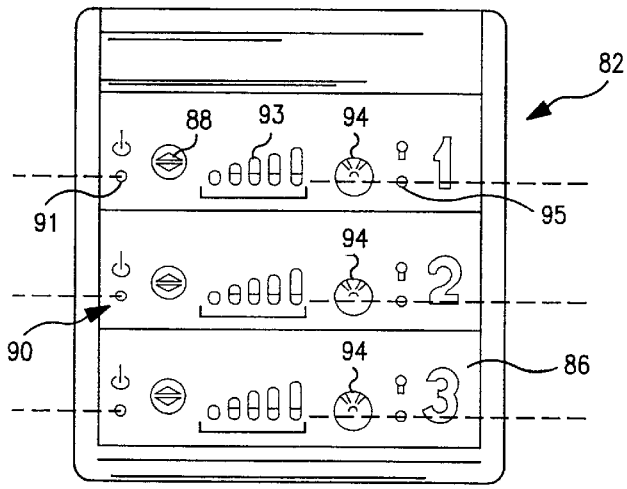
FIG. 4 is a front elevational view of another embodiment of the light-controller panel configured to control three separate surgical lights.
Figure 5:
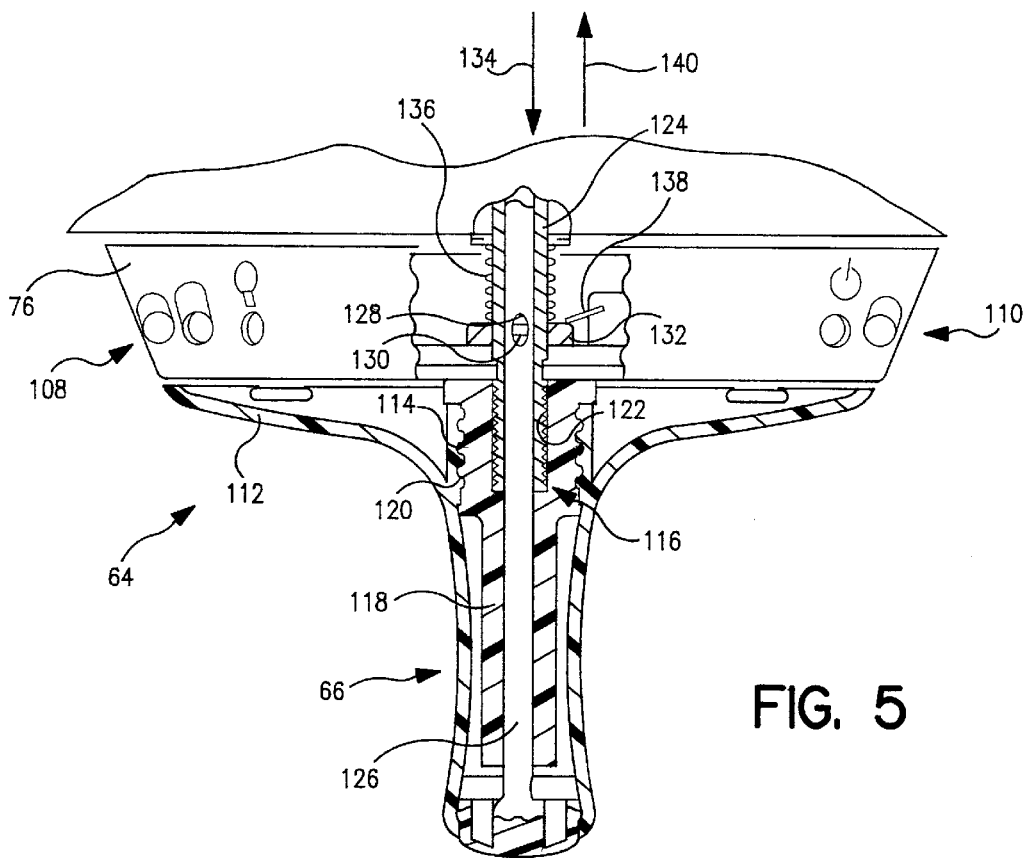
FIG. 5 is an enlarged view of the handle assembly of the present invention, with portions broken away to illustrate details of a push button actuator on the handle for controlling the intensity of light emitted from the surgical light apparatus.

FIG. 4 illustrates another embodiment of the wall controller box 82 which includes separate controls for three surgical lights. The controls and display indicators are the same as discussed above with reference to FIG. 1. Specifically, a standby mode indicator 91, lamp intensity indicators 93, and relamp indicator 95 are provided for each of the three surgical lights.

Further details of the handle assembly 64 are illustrated in FIGS. 5–9. Handle assembly 64 includes an elongated handle 66 having an integrally formed flange 112 which extends outwardly from the handle 66 toward the light core panel 76 to provide a smooth transition and cover adjacent the panel 76. Handle 66 further includes a threaded inner portion 114 configured to mate with threads 120 of an actuator assembly 116 located within handle 66. Actuator assembly 116 includes a support 118 having outer threads 120 configured to mate with threaded portion 114 of handle 66 and an inner threaded portion 122 configured to thread on to an end of actuator 124.

An elongated actuator rod 126 extends through a central aperture of support 118 and body 124. Rod 126 is formed to include an aperture 128 configured to receive a pin 130 therethrough. Pin 130 is coupled to washer 132. Washer 132 is biased downwardly in the direction of arrow 134 of FIG. 5 by a spring 136. Washer 132 abuts a switch 138 which is coupled to the controller 106 to adjust the intensity of the main bulb 68 or auxiliary bulb 70. Since washer 132 is coupled to actuator rod 126 by pin 130, movement of actuator rod 126 upwardly in the direction of arrow 140 of FIG. 5 causes actuation of switch 138 to adjust the intensity of bulbs 68, 70.

Figure 6:
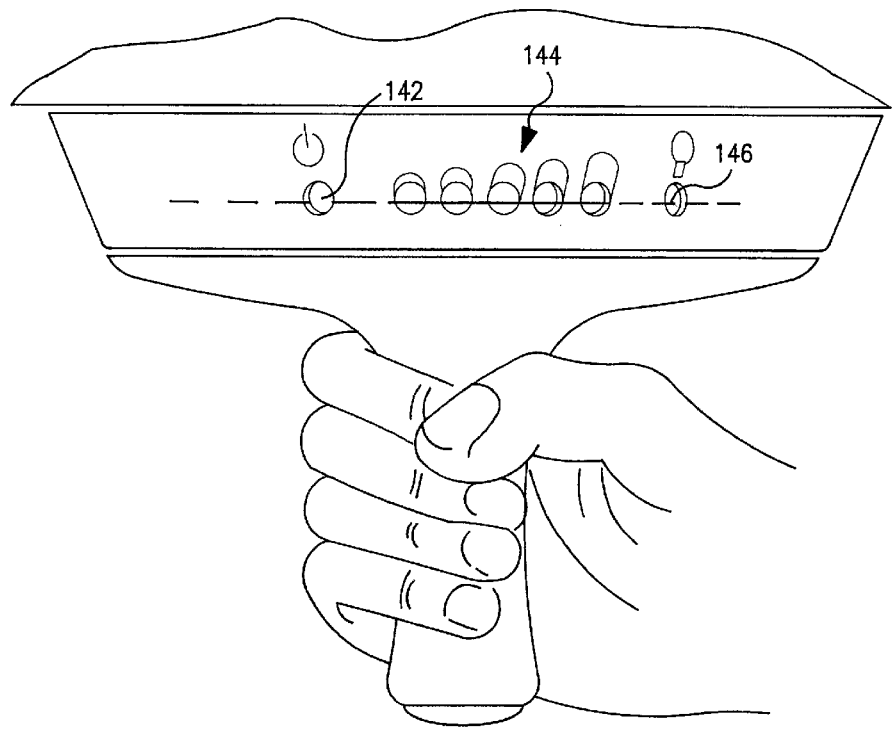
FIG. 6 is a side elevational view illustrating a surgeon gripping the handle to control movement of the surgical light and to adjust the size of a pattern of light generated by the surgical light, and illustrating a first display on the surgical light apparatus located above the handle.

As discussed above, controller 106 provides control signals to display readout LED's 108 and 110 on opposite sides of light core panel 76. Therefore, a surgeon can see the display regardless of the orientation of the surgical light. As illustrated in FIG. 6, the display LED's 108 and 110 include a first LED 142 indicating a standby condition when power is supplied to the surgical light. The next five LED's 144 provide an indication of the intensity level of light emanating from the bulb 68, 70. LED 146 provides a back-up bulb indicator which provides an indication that the auxiliary bulb 70 is in use. Therefore, an operator knows to replace the main bulb 68 at the earliest convenience.

Figure 7:
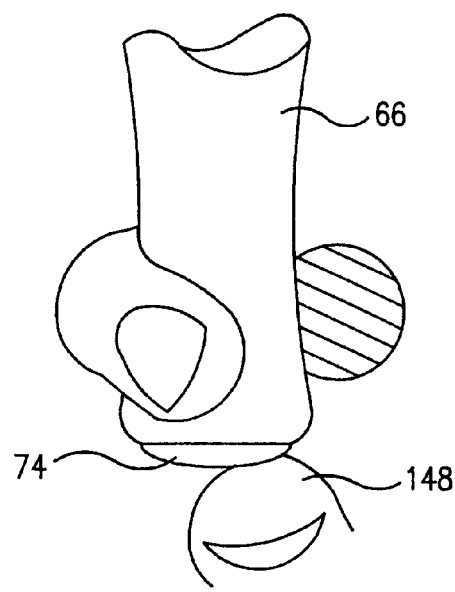
FIG. 7 is a partial view illustrating actuation of a control button on the handle by the surgeon to adjust the intensity of light emitted by the surgical light from a location within the sterile field.

The surgeon can grip the handle 66 as shown in FIG. 6 to adjust the location of the lighthead 36 and also can rotate the handle about its axis to adjust the pattern size of reflected light that illuminates the surgical site as discussed below. In addition, as illustrated in FIG. 7, the surgeon's thumb 148 is used to actuate the intensity control actuator 74 located at the distal end of handle 66 to turn the bulbs 68 or 70 on and off and to control the intensity setting of light emanating from bulbs 68, 70.

Various control techniques can be used with the single actuator 74 to control the intensity level of the bulbs 68, 70. First, a predetermined number of different intensity settings is selected. Illustratively, the present invention provides five different intensity level settings. In an illustrative operational sequence, the controller 106 turns on the bulb 68, 70 at full intensity when the actuator 74 is initially pushed. Each sequential push of the actuator 74 then decreases the intensity level by one setting. Once the lowest intensity level setting is reached, and the actuator 74 is pushed again, the surgical light controller 106 adjusts the bulb 68, 70 back to its highest intensity level. In order to turn off the light, the operator pushes the actuator 74 and holds the actuator depressed for a predetermined period of time, such as, for example, two seconds. It is understood that a different number of intensity level settings may be provided. In addition, the controller could be set to adjust the intensity level to a substantially infinite number of settings.

If desired, the light can be turned off with a quick press of the button as well. In other words, after the operator scrolls down to the lowest intensity level, the next push of the actuator 74 would turn the light off. Another control option is that the first actuator press turns the light bulb 68, 70 on at its lowest intensity level. Subsequent presses of the actuator 74 increase the intensity level up to the maximum level. In one embodiment, further short presses of the button do not change the intensity level, the operator must press and hold the actuator 74 so that controller 106 causes the light intensity to scroll down to lower settings at predetermined time intervals. For instance, after the light reaches its highest intensity, the operator can press and hold the actuator 74 and the controller 106 will automatically decrease the intensity level by one setting every predetermined interval, such as, for example, every one-two seconds. Once the actuator 74 is released, the operator can then scroll upwardly again using short actuator presses.

Other possibilities for controlling the intensity of bulbs 68, 70 are as follows, with intensity levels indicated from L1(lowest setting)–L5(highest setting). Each press of the actuator 74 moves the intensity to the next setting.

Option 1: Off-L1-L2-L3-L4-L5-L4-L3-L2-L1-Off.
Option 2: Off-L5-L4-L3-L2-L1-L2-L3-L4-L5-Off.
In both of these embodiments, the controller 106 could continue to scroll between the intensity levels without moving to the off position. The operator would then have to press and hold the actuator 74 for a predetermined period of time to turn the light off.

Figure 8:
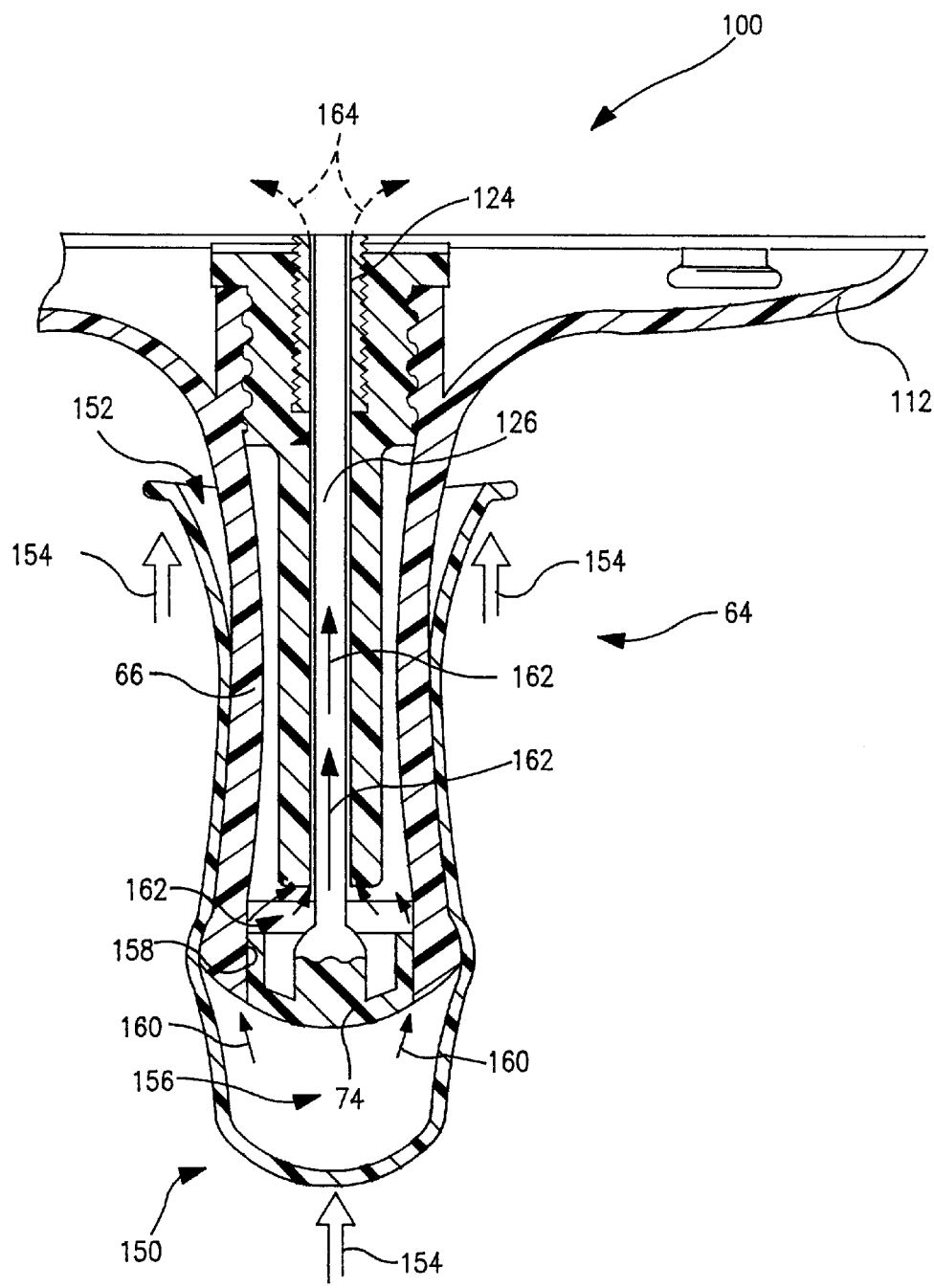
FIG. 8 is a sectional view through the handle of the present invention, illustrating initial insertion of a disposable cover or shield over the handle to provide a sterile field for the surgical procedure.
Figure 9:
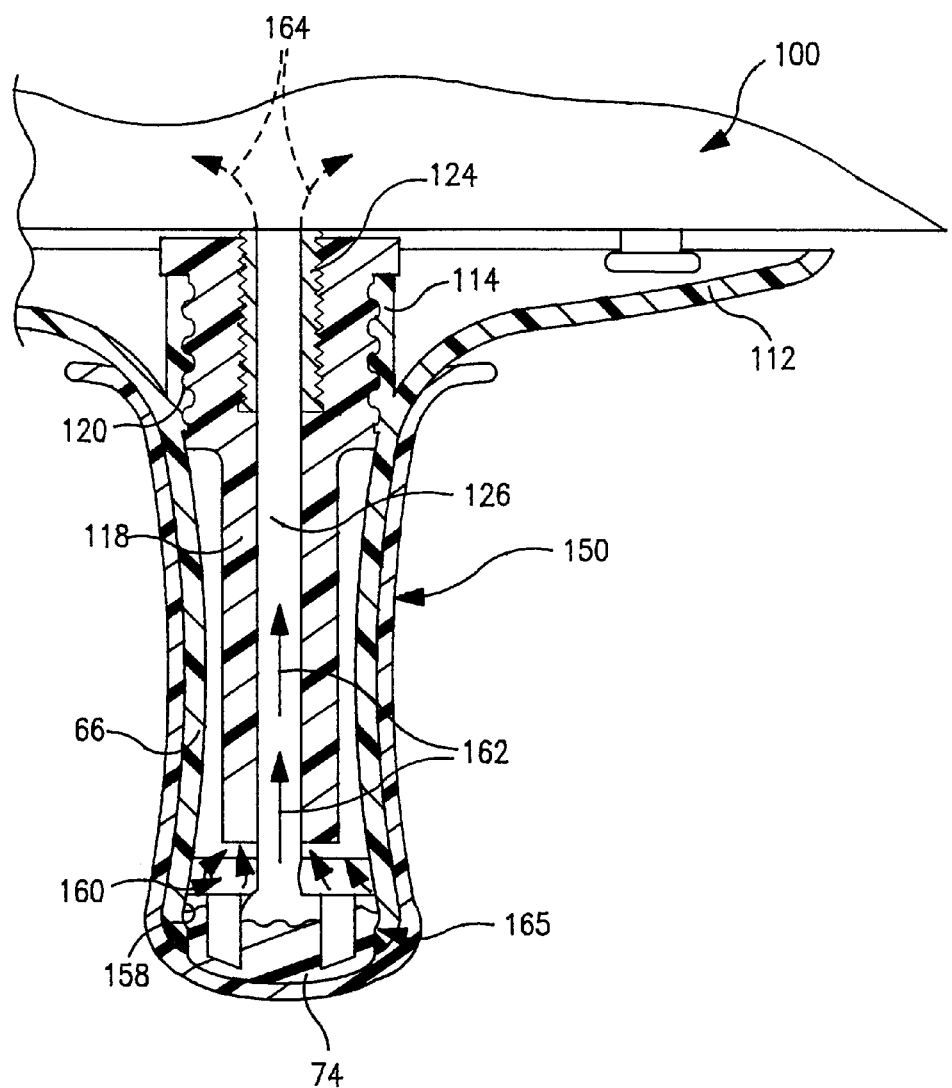
FIG. 9 is a sectional view similar to FIG. 8 illustrating the disposable shield fully mounted over the handle.

Another feature of the present invention is illustrated in FIGS. 8 and 9. The structure of the handle assembly 64 including the push button actuator rod 126 also facilitates installation of a disposable, sterile cover or shield 150 over the handle 66. The shield 150 includes an open end 152 which is configured to be inserted over the distal end of handle 66 in the direction of arrows 154 of FIG. 8. In conventional devices, air can become trapped in an interior region 156 between the shield 150 and the handle 66 as the shield 150 is inserted on to the handle 66.

In accordance with the present invention, the push button actuator 74 is located within an aperture 158 formed at the distal end of handle 66. As shown in FIG. 8, a space between actuator 74 and a sidewall defining aperture 158 of handle 66 permits air flow around the actuator 74 in the direction of arrows 160 as the shield 150 is inserted on the handle. Air flow continues upwardly through an interior region of the handle 66 as illustrated by arrows 162. Air can continue to flow upwardly past actuator rod 162 and out into the enclosure 100 within the light head 36 as illustrated by arrows 164. Because air is not trapped within region 156, cover 150 easily moves to the completely installed position shown in FIG. 9. Also as shown in FIGS. 8 and 9, the handle 66 includes an enlarged distal end portion 165 which provides a ridge to reduce the likelihood that the cover 150 will slip off the handle 66 during use.

Figure 10:
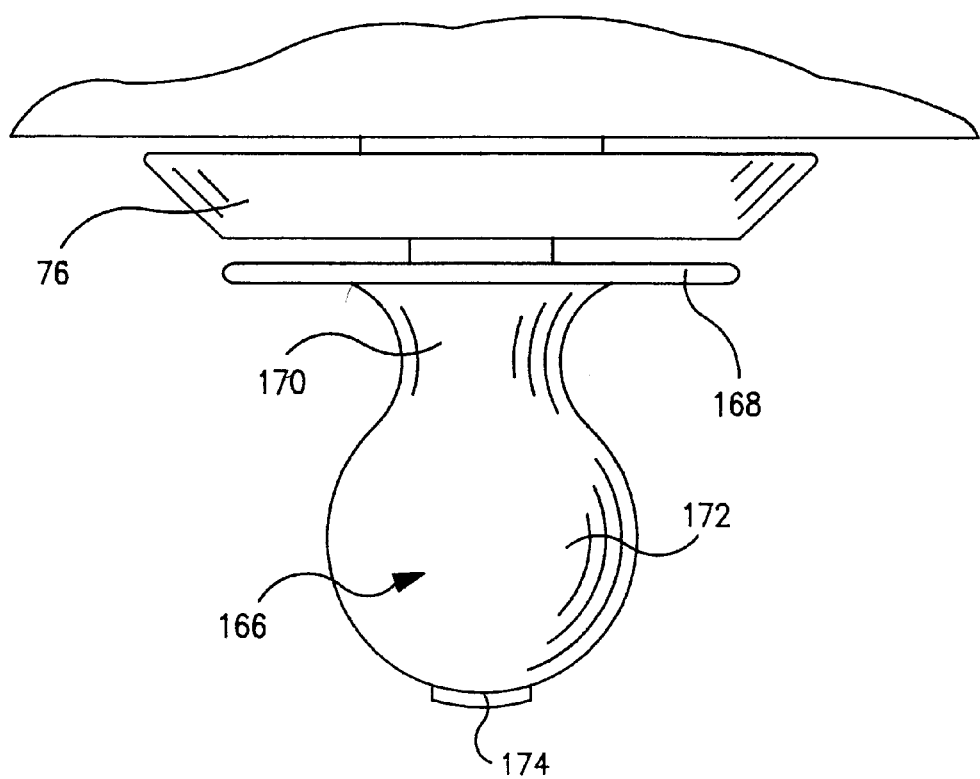
FIG. 10 illustrates another embodiment of the handle of the present invention.

FIG. 10 illustrates an alternative shape for the handle assembly of the present invention. In FIG. 10, the handle 166 includes a top plate 168 located adjacent panel 76, a thin neck portion 170, and an enlarged, bulbous portion 172. A push button actuator 174 is located adjacent a distal end of handle 166 to control the intensity of bulbs 68, 70, as discussed above.

Figure 11:
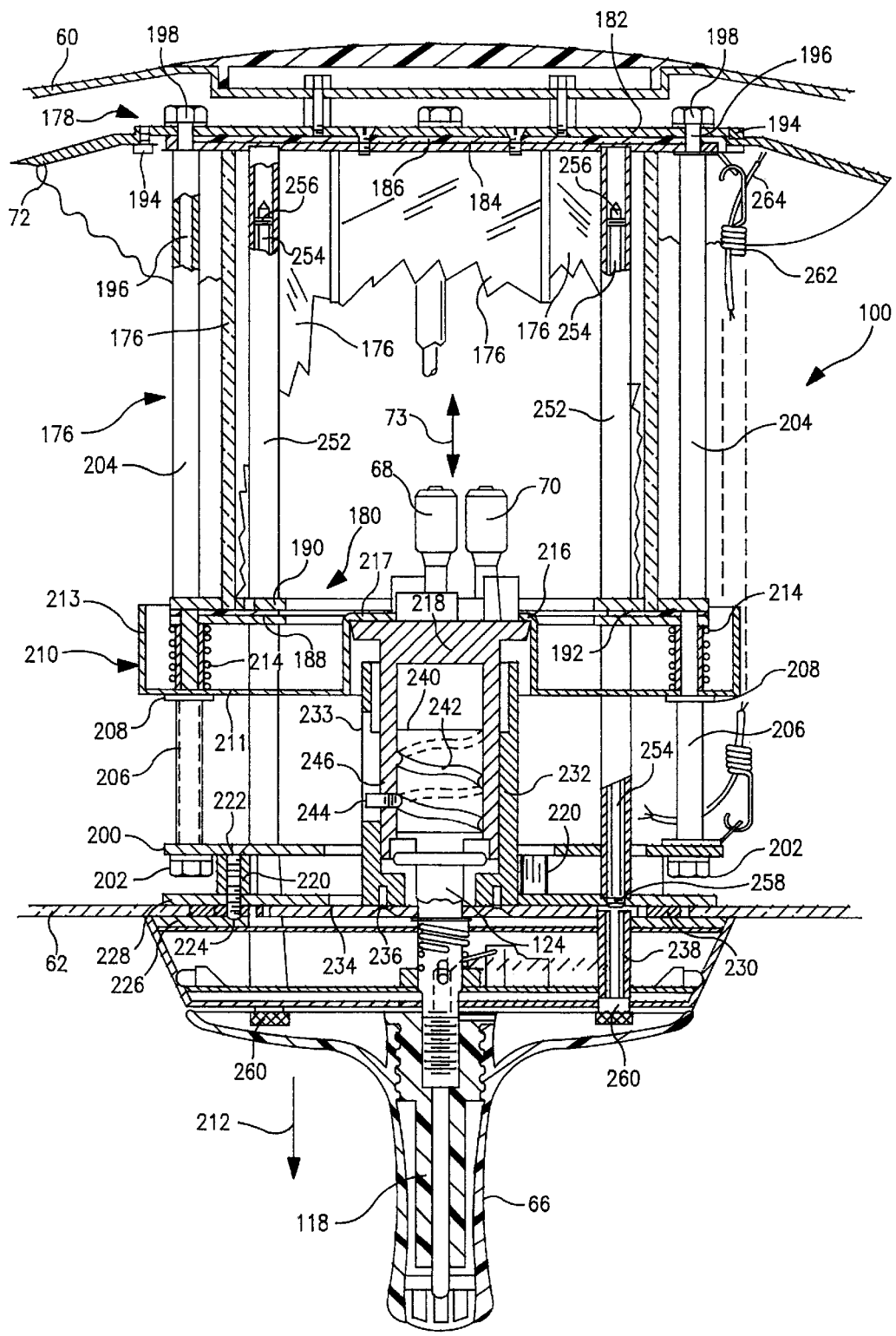
FIG. 11 is a sectional view taken through a portion of the surgical light apparatus illustrating structure for supporting a lamp assembly and a filter apparatus within an interior region of the surgical light.
Figure 12:
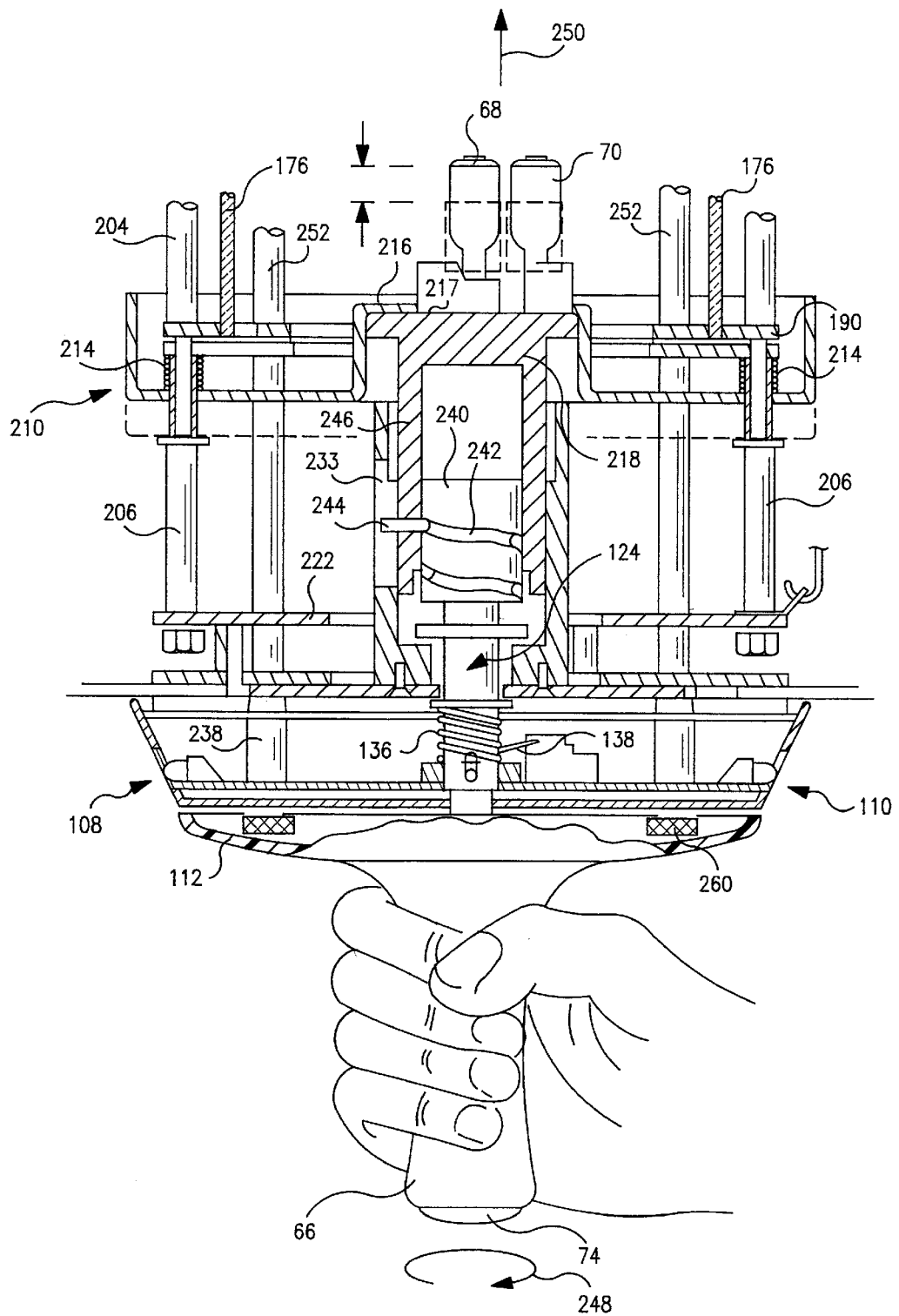
FIG. 12 is a sectional view of a portion of FIG. 11, illustrating movement of the main bulb and the auxiliary bulb upwardly relative to the reflector as a surgeon rotates the handle about its longitudinal axis.
Figure 13:
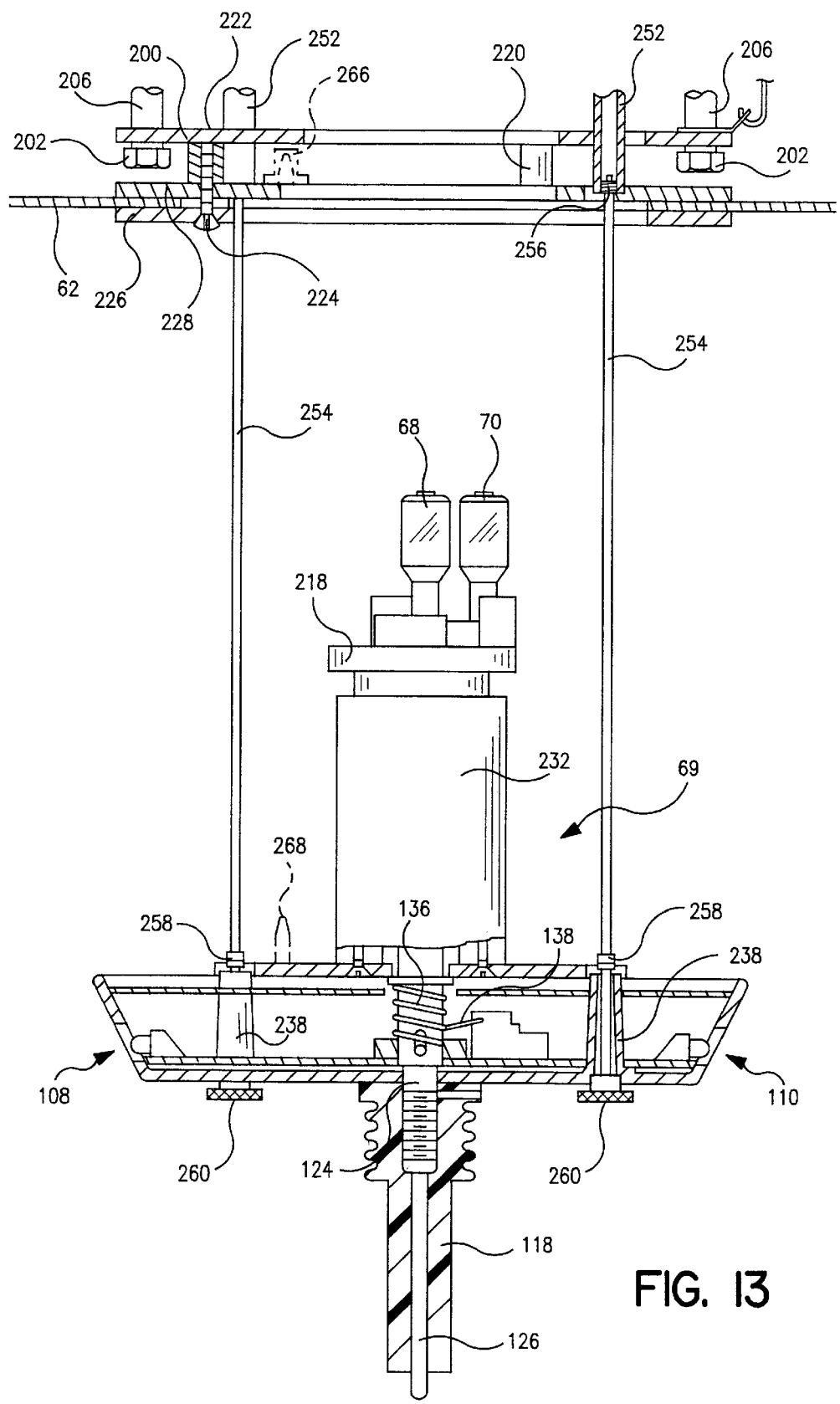
FIG. 13 is a sectional view illustrating movement of the handle and lamp assembly downwardly away from the rest of the surgical light apparatus to permit changing of the main bulb and the auxiliary bulb and to facilitate cleaning of the surgical light apparatus.

Further details of the structural components of the surgical light apparatus are illustrated in FIG. 11–13. A filter apparatus 71 is held in position within the enclosure 100. The filter apparatus 71 includes a plurality of spaced apart filter plates 176 configured to improve cooling of the surgical light apparatus as discussed in detail in co-pending application Ser. No. 09/050,529, now U.S. Pat. No. 6,443,596, incorporated by reference above.

Filter plates 176 are held in position by a top mounting apparatus 178 and a bottom mounting apparatus 180. Top mounting apparatus 178 includes a top plate 182, a bottom plate 184 formed to include filter plate-receiving slots, and a central gasket 186. Top ends of filter plates 176 enter the slots formed in bottom plate 184 and engage gasket 186. Similarly, bottom mounting apparatus 180 includes a bottom plate 188, a top plate 190 formed to include filter plate-receiving slots, and a gasket 192 located between the top plate 190 and bottom plate 188. Bottom ends of the filter plates 176 enter the slots formed in top plate 190 and engage gasket 192.

Top mounting apparatus 178 is secured to reflector 72 by fasteners 194. Threaded rods 196 are coupled at one end to top mounting apparatus 178 by fasteners 198. Opposite ends of threaded rods 196 are coupled to plate 200 by fasteners 202. First spacer tubes 204 are located over rods 196 between bottom plate 184 and top plate 190 of top and bottom mounting apparatus 178 and 180, respectively.

Spacer tubes 204 are sized to prevent excessive forces from being applied to filter plates 176 during installation. Bottom spacer tubes 206 are located adjacent plate 200. Washers 208 are located at a top end of spacers 206 to provide stops. An annular filament shield 210 is located above stops 208.

Filament shield 210 is biased downwardly in the direction of arrow 212 by springs 214. Filament shield 210 includes an inner flange 216 configured to engage a top surface 217 of lamp support 218. Lamps 68 and 70 are coupled to the top surface 217 of lamp support 218. Movement of lamp support 218 up and down to adjust the pattern of light is discussed below in detail.

The filament shield 210 is configured to shield both the primary lamp 68 and redundant lamp 70 so that light emitted from the lamps 68, 70 strikes the reflector 72. In other words, light from lamps 68, 70 cannot pass directly through the lens 62 before the light hits reflector 72. The filament shield 210 moves up and down with the lamp support 218 in the direction of doubleheaded arrow 73 during pattern change adjustment to provide filament shielding through the entire range of movement of the lamp assembly 69. When the lamp assembly 69 is moved out from the lighthead core during bulb replacement or maintenance as shown in FIG. 13, the filament shield 210 remains part of the lighthead core. In other words, while the filament shield 210 moves up and down with the primary lamp 68 and redundant lamp 70 during pattern adjustment, the filament shield 210 remains inside the interior region 100 of the lighthead 36 when the lamp assembly is removed for lamp replacement or maintenance. The shape of the filament shield 210 provides shielding for both the primary bulb 68 and redundant bulb 70. Shield 210 includes a bottom plate 211 and an outer sidewall 213 extending upwardly from an edge of bottom plate 211.

Plate 200 is coupled to spacers 220 by fasteners 222. Opposite ends of spacers 220 are coupled to a pair of plates 226 and 228 which are located on opposite sides of the lens 62. A gasket 230 is located between the plates 226 and 228.

A cylindrical outer support 232 is coupled to a plate 234 by fasteners 236. Plate 234 is formed to include apertures which receive tube segments 238 therein. Actuator body 124 includes a head portion 240 having a helical groove 232 formed therein. A set screw 244 extends through a slot 233 formed in cylindrical support 232 and is coupled to a sidewall 246 of lamp support 218. The set screw 244 engages the helical groove 242. Therefore, as handle 66 is rotated about its longitudinal axis as illustrated by arrow 248 of FIG. 12, the actuator body 124 rotates and set screw 244 moves in the groove 242 so that the lamp support 218 moves upwardly in the direction of arrow 250 of FIG. 12. This changes the relative position of the bulbs 68, 70 relative to the reflector 72 to change the pattern size of reflected light that illuminates the surgical site. FIG. 12 illustrates the support 218 in its uppermost position. Spring 214 is compressed by movement of the frame upwardly in the direction of arrow 250 away from stops 208. Filter apparatus 71 does not move when the bulbs 68 and 70 move upwardly in the direction of arrow 250.

The surgical light apparatus further includes a set of four spacer tubes 252 extending between bottom plate 184 of top mounting apparatus 178 and plate 228 located adjacent lens 62. Extension rods 254 are located within tubes 252. Rods 254 have a first set of threads 256 coupled to a first end. Another set of threads 258 couple to the rods 254 and an actuator 260 is rigidly coupled to a second end of rods 254. Plate 228 includes threaded apertures for receiving threads 258 and 256.

When the surgical light apparatus is in its normal operating position, threads 258 engage the threaded apertures formed in plate 228 to secure the handle assembly 64 in its fixed position relative to the remainder of the lighthead 36. When it is necessary to change a bulb 68, 70, or to obtain access to an interior region of the lamp for cleaning or other purpose, handle 66 is first unscrewed from support 118 to expose the actuators 260 coupled to rods 254. Actuators 260 are then rotated about a longitudinal axis of rods 254 to remove the threads 258 from the threaded apertures of plate 228.

After the threads 258 are released from plate 228, the rods are free to slide downwardly in the direction of arrow 212 relative to the lens 62 to the extended position shown in FIG. 13. This extended position provides access to the lamp assembly 69 for changing bulbs 68, 70 as well as for inspection and cleaning.

Further rotation of actuators 260 about the longitudinal axis of rods 254 removes the top threads 256 from threaded apertures in plate 228 so that the entire handle assembly 64 and light assembly 69 can be removed from the remainder of the surgical light. Threads 256 are sized to hold the light assembly 69 in the position of FIG. 13, unless the rods 254 are rotated to release the threads 256 from plate 226.

After the bulbs 68, 70 are changed, the support 118 can be lifted upwardly so that the rods 254 slide back into the tubes 252 to the position shown in FIG. 11. Actuators 260 are then rotated in an opposite direction so that lower threads 258 on rods 254 enter the threaded apertures of plate 228 to secure the lamp assembly 69 to the remainder of the surgical light as shown in FIG. 11.

As also shown in FIG. 11, a spring 262 is connected between plate 184 and plate 200. An interior region of the spring 262 provides a conduit for routing an electrical wire 264 through the enclosure 100. The spring 262 does not provide any biasing or lifting forces since the plates 184 and 200 remain in the same relative position. The electrical wire 264 is routed through the spring 262 to a first electrical connector 266 located adjacent plate 228. Lamp assembly 69 includes a second electrical connector 268 which automatically mates with the first connector 266 when the lamp assembly 69 is moved to its upward operational position shown in FIG. 11. This automatic mating of electrical connectors 266 and 268 permits electrical power to be supplied to the bulbs 68, 70 without a wire 264 being attached to the movable portion of the lamp assembly 69. Therefore, wire 264 does not move outwardly from the enclosure 100 when the lamp assembly 69 is moved outwardly to the extended position of FIG. 13.

Although the invention has been described in detail with reference to a certain illustrated embodiment, variations and modifications exist within the scope and spirit of the invention as described and as defined in the following claims.

What is claimed is:

1. A surgical light apparatus comprising a reflector, a lens coupled to the reflector, a bulb located between the reflector and the lens, a handle located adjacent the lens, a controller coupled to the bulb, and an actuator coupled to the controller to adjust an intensity level of light emitted from the bulb, the actuator being located on the handle, the handle being configured to define an air passage to facilitate installation of a shield over the handle.

2. The apparatus of claim 1, wherein the handle includes a longitudinal axis and a distal end, the air passage being formed in the distal end of the handle and extending along the longitudinal axis.

3. The apparatus of claim 2, wherein the distal end of the handle is enlarged to retain the shield on the handle.

4. The apparatus of claim 1, wherein the handle is located within a sterile field of the apparatus.

5. The apparatus of claim 1, wherein the actuator extends through an interior region of the handle defined by an aperture formed along a longitudinal axis of the handle, the air passage being formed between the handle and the actuator.

6. The apparatus of claim 1, wherein the air passage extends into an interior region of the apparatus formed between the reflector and the lens.

7. A surgical light apparatus comprising a reflector, a lens coupled to the reflector, a bulb located between the reflector and the lens, and a handle located adjacent the lens, the handle being configured to define an air passage to facilitate installation of a shield over the handle, the handle being configured to be rotated about a longitudinal axis to move the bulb relative to the reflector.

8. A surgical light apparatus comprising a lighthead including a bulb, a lens, a controller for turning the bulb on and off and for adjusting an intensity level of light emitted from the bulb, a first display, and second display spaced apart from the first display, the first display and second display each being coupled to the controller and each being configured to display an indication of the intensity level of the bulb.

9. The apparatus of claim 8, wherein the first and second displays are spaced apart by about 180°.

10. The apparatus of claim 8, wherein the first and second displays each include a plurality of LEDs, each LED indicating a different light intensity level for the bulb.

11. The apparatus of claim 8, wherein the first and second displays also include an indicator that electrical power is supplied to the apparatus.

12. The apparatus of claim 8, wherein the apparatus includes a main bulb and an auxiliary bulb, and the first and second displays each include an indicator that the main bulb is burned out.

13. The apparatus of claim 8, wherein the first and second displays are located in a sterile field of the apparatus.

14. A surgical light apparatus comprising a lighthead including a reflector, a lens coupled to the reflector, a plurality of tubes mounted in an interior region of the lighthead between the reflector and the lens, a lamp assembly including a support and at least one bulb, and a plurality of rods configured to engage the support, each rod being configured to extend through the support and into a corresponding tube, the rods including at least one threaded portion configured to secure the lamp assembly within the interior region, the rods being slidable relative to the tubes upon disengagement of the threaded portion of the rods to permit the lamp assembly to move out of the interior region of the lighthead, the rods each being formed to include a stop to prevent separation of the lamp assembly from the lighthead.

15. The apparatus of claim 14, wherein the stops are threaded stops so that the rods can be removed upon rotation of the rods to permit separation of the lamp assembly from the lighthead.

16. A surgical light apparatus comprising a lighthead including a reflector and a lens, a lamp assembly including a support and at least one bulb located on the support, a lamp position adjustment mechanism which is coupled to the support and configured to adjust a position of the lamp assembly relative to the reflector to change a pattern size of reflected light emitted from the apparatus, and a filament shield mounted in an interior region of the lighthead between the reflector and the lens to block light from passing from the at least one bulb directly through the lens, the filament shield being configured to move with the lamp assembly as the position of the lamp assembly is adjusted by the lamp position adjustment mechanism, and the filament shield also being configured to remain in the interior region of the lighthead when the lamp assembly is removed from the interior region.

17. The apparatus of claim 16, further comprising a frame mounted to the lighthead between the reflector and the lens, the filament shield being coupled to the frame.

18. The apparatus of claim 17, wherein the frame includes a stop, the filament shield being mounted between the stop and the reflector to provide a limit position for movement of the filament shield toward the lens, the filament shield being spring biased against the stop.

19. The apparatus of claim 18, wherein the filament shield includes an inner flange configured to engage the support of the lamp assembly, the lamp assembly being configured to move the filament shield away from the stop as the position of the lamp assembly is adjusted by the lamp position adjustment mechanism.

20. The apparatus of claim 16, wherein the lamp assembly includes a primary bulb and a redundant bulb, the filament shield being configured to block light from both the primary bulb and the redundant bulb from passing directly through the lens.

21. The apparatus of claim 20, wherein the filament shield includes a bottom plate and an outer sidewall extending upwardly from an edge of the bottom plate.

22. A surgical light apparatus comprising a reflector, a lens coupled to the reflector, a bulb located between the reflector and the lens, a handle located adjacent the lens, a controller coupled to the bulb, and an actuator coupled to the controller to adjust an intensity level of light emitted from the bulb, the actuator being located on the handle.

23. A surgical light apparatus comprising a reflector, a lens coupled to the reflector, a bulb located between the reflector and the lens, and a handle located adjacent the lens, the handle being configured to be rotated about a longitudinal axis to move the bulb relative to the reflector.

24. A surgical light apparatus comprising a lighthead including a reflector, a lens coupled to the reflector, a plurality of tubes mounted in an interior region of the lighthead between the reflector and the lens, a lamp assembly including a support and at least one bulb, and a plurality of rods coupled to the support, each rod being configured to extend into a corresponding tube, the rods including at least one threaded portion configured to secure the lamp assembly within the interior region, the rods being slidable relative to the tubes upon disengagement of the threaded portion of the rods to permit the lamp assembly to move out of the interior region of the lighthead, the rods each being formed to include a stop to prevent separation of the lamp assembly from the lighthead.

25. A surgical light apparatus comprising a lighthead including a reflector and a lens, a lamp assembly including a support and at least one bulb located on the support, a lamp position adjustment mechanism which is coupled to the support and configured to adjust a position of the lamp assembly relative to the reflector to change a pattern size of reflected light emitted from the surgical light apparatus, and a filament shield mounted in an interior region of the lighthead between the reflector and the lens to block light from passing from the at least one bulb directly through the lens, the filament shield being configured to move with the lamp assembly as the position of the lamp assembly is adjusted by the lamp position adjustment mechanism.

\* \* \* \* \*